United States Patent [19]

Lundström et al.

[11] Patent Number: 4,521,522

[45] Date of Patent: Jun. 4, 1985

[54] OPTICAL SPECIFIC BINDING ASSAY WITH REFLECTION OF POLARIZED ELECTROMAGNETIC RADIATION

[75] Inventors: Kurt I. Lundström, Faergaregatan 10, S-582 52 Linkoeping, Sweden; Hans R. Arwin, Linkoeping, Sweden; Erwin Rieke, Seeheim-Jugenheim, Fed. Rep. of Germany; Günter Sielaff, Bensheim, Fed. Rep. of Germany; Norbert Hennrich, Darmstadt, Fed. Rep. of Germany

[73] Assignee: Kurt I. Lundstroem, Linkoping, Sweden

[21] Appl. No.: 415,510

[22] Filed: Sep. 7, 1982

[30] Foreign Application Priority Data

Sep. 5, 1981 [DE] Fed. Rep. of Germany ....... 3135196

[51] Int. Cl.³ .................... G01N 33/54; G01N 33/78; G01N 21/21
[52] U.S. Cl. .................... 436/525; 356/364; 436/164; 436/500; 436/527; 436/531; 436/805
[58] Field of Search ............... 436/525, 527, 531, 805

[56] References Cited

U.S. PATENT DOCUMENTS 2,666,355   1/1954   Trurnit .
3,770,380  11/1973   Smith ............................ 436/805 X
3,905,767   9/1975   Morris ........................... 436/805 X
3,939,350   2/1976   Kronick ......................... 436/805 X
3,973,129   8/1976   Blumberg ....................... 436/805 X
4,054,646  10/1977   Giaever ......................... 436/805 X
4,317,810   3/1982   Halbert .......................... 436/531

*Primary Examiner*—Sidney Marantz
*Attorney, Agent, or Firm*—Millen & White

[57] ABSTRACT

A process, means and devices for the quantitative determination, using electromagnetic radiation, of a component of a group including specifically bonding receptors and substances which can be specifically bonded by these receptors are based on a process comprising incubating one of the components, after it is immobilizing on the surface of a material having refractive index different from that of the components, with the other particular component and, optionally, further components, which can be labelled; irradiating the surface with electromagnetic radiation which is polarized parallel to the plane of incidence, the angle of incidence of the radiation being approximately equal to the angle Φ at which the intensity of the radiation reflected from the uncoated or precoated surface reaches a minimum; and ascertaining the intensity of the reflected radiation as a measure of the concentration to be determined.

11 Claims, 3 Drawing Figures

OPTICAL SPECIFIC BINDING ASSAY WITH REFLECTION OF POLARIZED ELECTROMAGNETIC RADIATION

BACKGROUND OF THE INVENTION

The present invention relates to processes, means and devices using electromagnetic radiation for the determination of a component of a group of specifically bonding receptors and substances which can be specifically bonded by these receptors, in particular to processes, means and devices for the immunological determination of antibodies, antigens and haptens.

The most usual processes for sensitive immunological determination of antibodies, antigens and haptens are based on the use of labelling substances, such as radioisotopes, enzymes or fluorochromes, which are coupled chemically to one of the components. The necessity of coupling antibodies, antigens or haptens to such a labelling substance has, however, a number of substantial disadvantages: chemical linking of an antibody (antigen) to, for example, an enzyme produces interference in the bonding properties of the antibody (antigen), i.e., its bonding affinity decreases; chemical linking of an enzyme to an antibody (antigen) leads to a substantial reduction in the enzymatic activity; the stability of the conjugates is lower than the stability of the individual substances; the conjugates are very heterogeneous compounds with a broad molecular weight spectrum, so that reproducible preparation is made extremely difficult; and for bonding of conjugates to a solid phase, the enzymatic activity is affected by diffusion of substrates and products.

Because of such disadvantages, there is a need for simpler methods, for example enabling direct measurement of the immunological reaction. Such processes are already known, but are either not sensitive enough, as in the case of turbidity measurements, or too expensive and too complicated, as in the case of determination of antigen-antibody layers on metal surfaces by ellipsometry.

A measurement arrangement for the determination of thin layers, which is somewhat simplified in comparison with a conventional ellipsometer, is described in European Patent Application 19,088, wherein essentially only the compensator of an ellipsometer is replaced by a reference surface. German Offenlegungsschrift 2,638,250 describes a simple process for measuring antigen-antibody layers on glasses coated with metal beads. This certainly by-passes the difficulties of ellipsometry, but only provides semi-quantitative information.

SUMMARY OF THE INVENTION

It is an object of the present invention to provide processes, means and devices for the determination of antibodies, antigens and haptens, with which the disadvantages described can be avoided.

Upon further study of the specification and appended claims, further objects and advantages of this invention will become apparent to those skilled in the art.

These objects have been achieved by this invention, by immobilizing one of these components on a reflecting surface, incubating it with the component to be determined, irradiating the system and determining the concentration based on the reflected radiation.

The present invention relates to a process for the quantitative determination, using electro-magnetic radiation, of a component of a group consisting of specifically bonding receptors and substances which can be specifically bonded by these receptors, comprising incubating one of the components, after it is immobilized on the surface of a material having a refractive index different from that of the components, with the other particular component and, optionally, further components which can be labelled; irradiating the surface with electro-magnetic radiation which is polarized parallel to the plane of incidence, the angle of incidence of the radiation being approximately equal to the angle $\Phi$ at which the intensity of the radiation reflected from the uncoated or precoated surface reaches a minimum; and determining the intensity of the reflected radiation as a measure of the concentration to be determined.

The invention furthermore relates to a means (e.g., a kit) for carrying out this process, containing platelets or small discs of the material, on the surface of which one of the components is immobilized, and, usually, standard solutions of known concentrations of the component to be determined and optionally further components, which can be labelled.

The invention moreover relates to devices for carrying out the process, comprising a block (1) for accommodating a light source housing (2) and a detector housing (3), the optical axes (5) and (6) of both units intersecting the surface, to be investigated, of the material (4) at an angle $\Phi$ to be perpendicular to the surface, and the light source housing (2) or the detector housing (3) containing a polarization filter (7) which lets through for evaluation only the part of the radiation which is polarized parallel to the plane of incidence.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

Figure 1:
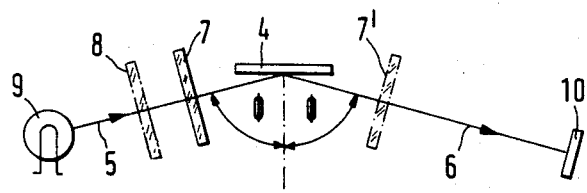
FIG. 1 schematically illustrates a device for carrying out the method of this invention.

Surprisingly, it has been found that the process according to this invention provides a very simple quantitative detection of immunological reactions in that the determination of the ellipsometric angle is obviated and is replaced with a purely photometric detection in which neither manipulations of the instrument, such as changes of the angle of incidence or rotation of the polarizers or of the compensator, nor involved calculations for the determination of the desired concentration are necessary. The process can be carried out with little technological effort and the devices required are quite substantially smaller, cheaper, less susceptible to breakdown and simpler to operate than the ellipsometric devices known hitherto. Moreover, the process gives concentration-proportional measurement values for incubated platelets or small discs in an extremely short time, which means that it is also particularly suited to automation and to simultaneous determination of several immunological parameters.

A prerequisite for the process according to this invention is that the refractive index of the material, on the surface of which the antigen/hapten or the antibody is to be immobilized, differs significantly from the refractive index of the antigen/hapten-antibody layer to be measured, and that for the material there is a clear minimum in the plot of the reflection coefficients for radiation polarized parallel to the plane of incidence against the angle of incidence $\Phi$. Such plots can be found e.g. in R. M. A. Azzam and N. M. Bashara "Ellipsometry and Polarized Light" 1979, 2nd ed. North-Holland Publishing Company, Amsterdam•New York•Oxford. In general, the refractive index of the compounds attached to the surface of the material should differ from the refractive index of the material by at least 10%.

For the angle of incidence, the surface coated with the antigen/hapten-antibody layer is preferably irradiated with monochromatic light generated e.g. by colored glass filters; the intensity of the light reflected from the surface, namely that part which is polarized parallel to the plane of incidence, is measured. Equivalently, the impinging radiation can be polarized as required and the full reflected intensity measured, or the impinging radiation can be randomly or otherwise polarized and only the intensity of reflected radiation polarized parallel to the plane of incidence measured. Similarly, this impinging light can be monochromatic or the detector can be made to respond only a selected bandwidth of this impinging radiation.

The wavelength of radiation should be selected such that the substrate material and the applied layers have the necessary optical properties described herein. Typically, but without limiting this invention, the radiation will be in the visible/IR range, i.e., 200–2000 nm. Impinging intensities are fully conventional for reflectance systems and are routinely selected in accordance with the optical characteristics of the system used.

As far as the attached organic layer (e.g., antigen/hapten-antibody) per se is concerned, the specific relationships among the optical properties of each of the components forming the attached layer will not be critical in general and this invention will have wide applicability, e.g., to organic systems.

That is, the refractive indices of the various components of the attached layer will be relatively much closer to one another than to the refractive index of the substrate; thus, for the version of this invention which depends solely upon the effect of the components per se of the antigen/hapten-antibody system, and effect is primarily due to the thickness of the attached layer. In general, maximum increases in intensity will be observable for layers to be determined which have a thickness smaller or equal to the wavelength of the impinging radiation. The apparent thickness of molecules on the surface is given by the molecular diameter times the area covered by the molecules divided by the total area of the surface to be measured.

To increase the sensitivity of the measurement the angle of incidence is selected to provide a minimum in the reflectivity curve of the reflecting surface of the material thus providing a low base line value.

Suitable materials for immobilizing the components are those which have a flat reflecting surface and a refractive index greater than 1.5, preferably greater than 2. The material can be opaque or transparent to the radiation used. Above all, semi-conductors, dielectrics, metals or carriers coated therewith can be used for this purpose. Preferred materials include semiconductors, such as silicon or germanium, glasses, plastics, for example polymethylmethacrylate or polystyrene, and, in particular, carriers of glass or plastic which are coated with silicon and any desired carriers which are coated with a layer of metal.

The surface of the chosen material can be precoated before immobilization of one of the mentioned components. It is thus possible, for example, to coat the surface with a thin polymer film which is particularly suitable for subsequent immobilization of one of the components (Chemtech. 7, 766–778 (1977)) whose disclosure is incorporated by reference herein. It is furthermore possible, for example if silicon or germanium is used, to apply a thin layer of oxide to the surface. One of the components can then be immobilized on this oxide layer in a manner which is known per se, if necessary after chemical activation of the oxide. On the other hand, this oxide layer can also be reacted with reactive silanes, in which case the immobilization can also be carried out by chemical reaction with silane groups which are still reactive. As well as being suitable for the immobilization, the preformed thin layer on the surface of the material also leads to an increase in the detection sensitivity of the process according to this invention.

To carry out the process, an antigen/hapten layer or an antibody layer is immobilized on the surface of a material described above. This is most simply effected by incubating the surface of the material, which has preferably been cleaned, with a solution of the component to be determined. Incubation conditions are fully conventional. If the layer thus formed is brought into contact with an antibody solution or an antigen/hapten solution, the first layer bonds specifically to one part of the molecules from this solution, so that a more or less pronounced second layer forms on the first layer. The degree of coverage in this second layer depends on the concentration of the molecules in the particular solution and on the incubation period. It has been found, surprisingly, that if the material for immobilizing the antigen/hapten layer or the antibody layer and a defined angle of incidence are suitably chosen as required by this invention, the degree of coverage in the second layer can be measured by simply measuring the intensity of the light reflected from the surface provided that light which, before and/or after reflection, has been polarized parallel to the plane of incidence is used.

In principle, all organic substances for which a bonding partner exists can be determined quantitatively by the process according to this invention. Thus, for example, determination in the systems hormone-hormone receptor, lectin-saccharide, lectin-glycoprotein, enzyme-enzyme inhibitor or similar systems can also be carried out in an analogous manner to those described herein in terms of antibody-antigen/hapten systems. As long as the conditions described herein are met, any such system can be used.

In addition to determining the concentration of one of these components by measuring the intensity of the reflected radiation in the presence of the second layer, other variants of the process according to this invention can also be carried out. Thus, the determination of haptens can be facilitated by allowing the hapten to be determined to compete for bonding to the surface of bonded antibodies with a conjugate of the hapten and another immunochemically inert substance of large volume. In this case, the substance of large volume bonded to the antibody layer causes an increase in the signal. The hapten per se does not, since it does not effectively contribute a sufficiently large increase in the size of the second layer. The intensity of the reflected light is thus inversely proportional to the concentration of the hapten in the solution under investigation.

A further modification comprises a procedure in which the hapten in the solution under investigation is allowed to react with a known amount of antibody and the remaining antibody still not complexed is then reacted with hapten bonded to the surface. It is also possible in this procedure first to label the antibody used with a substance of large volume, such as ferritin, or with particles such as latex particles, in order to obtain an intensification of the signal.

In another variant, the process according to the invention can also be carried out by the so-called sandwich methods. In this method, the antigen in the solution under investigation first reacts with the antibody bonded to the surface. In a further reaction, the resulting (partial) double layer can be reacted with the same antibody or with another antibody directed towards the antigen, a triple layer being obtained. This antibody can also be labelled with a molecule of large volume or a particle, it also being possible for the selected particles to be metal particles. The possibilities of intensifying the signal by one or more antibodies directed against the already bonded component or by other components which bond to the already bonded component or are bonded by these components are not restricted to the above examples; it is also possible, for example, to use other bonding systems, such as avidin/biotin or glycoprotein/lectin.

The means according to the invention comprising platelets (e.g., 2–40×2–20×0.1–1 mm) or small discs of the above material, on the surface of which a layer of one of the components is immobilized. Most usually, there are also included standard solutions with known concentrations of the other component and, optionally, a solution of one of the components, which can be conjugated with a third voluminous molecule. The constituents are preferably in the form of a test pack or kit. Details can be readily determined with a knowledge of the ultimate test system's characteristic features.

Figure 2:
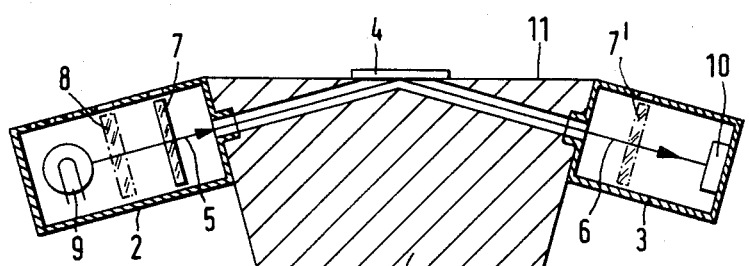
FIG. 2 illustrates a particularly simple and compact version of the device of this invention.
Figure 3:
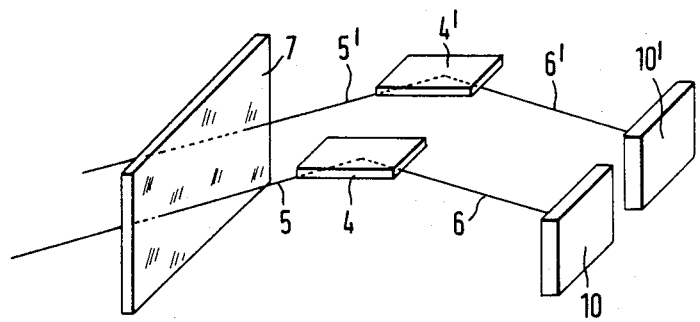
FIG. 3 illustrates an embodiment of the invention useful for the determination of more than one system.

The device with which the process according to the invention can be carried out is distinguished by its very simple and compact design; it is illustrated in more detail in FIGS. 1 to 3. FIG. 1 shows a schematic representation of such a device, and FIGS. 2 and 3 show advantageous embodiments.

The device shown in FIG. 1 comprises a light source (9), a polarization filter (7) and a photodetector (10), the angle of incidence Φ and the transmission direction of the polarization filter (7) being adjusted such that the detector (10) is a minimum for a particular uncoated or precoated material (4). Under the above-mentioned conditions, the polarization filter (7) can, of course, also be located in beam (6) instead of beam (5); if 2 polarization filters (7) and (7') are used, the transmission direction of the analyzer (7') is to be selected perpendicular to the plane of incidence. Furthermore, it is preferable, although not essential, to introduce a monochromator (8), for example a filter, into beam (5) or to use a narrow-band radiation source (9) or a narrow-band detector (10).

The advantageous embodiment of the invention shown in FIG. 2 comprises a block (1), which has a bore in each case under the angle of incidence and angle of reflection to accommodate the light source housing (2) and the detector housing (3), the optical axes (5) and (6) intersecting in the support plane (11) for the material (4). If the material used is silicon, which is obtainable with the desired flat, highly reflective surface, only an incandescent lamp (9), the polarization filter (7) and a lead sulphide infra-red detector, as an example of a narrow-band photoreceiver (10), are required as the optical components of the device according to this invention. Lasers, laser diodes and the like are also suitable light sources.

Another particularly advantageous embodiment is shown in FIG. 3. The simple, compact design of the device according to this invention enables two materials (4) and (4') to be irradiated simultaneously with two partial beams (5) and (5') with one and the same alignment of the polarization filter (7) and the reflected partial beams (6) and (6') to be detected simultaneously with 2 detectors (10) and (10'). Relative measurement of two materials (4) and (4') which are coated with different receptors but are otherwise the same is thereby possible, and the selectivity of the determination is thus increased. Moreover, the device according to this invention provides the possibility of simultaneous determination of a large number of receptor and substance groups with a correspondingly large number of partial beams.

In addition to the exemplary embodiments described for the device, other photometric, techniques which are known per se can, of course, also be used; thus, relative measurements can also be carried out on one and the same small disc of material or multi-component determinations can also be carried out on several small discs by scanning the light beam or by scanning the small material disc(s), and methods of improving the signal/-noise ratios, for example by alternating light amplifiers with phase tuning or in-phase amplifiers which are synchronized with the modulation frequency, can be applied.

A further advantage of the device according to the invention is that mechanization is simple to effect; by shifting or rotating the material (4) on the support plane (11), a large number of small discs of material can be measured with little effort, without expensive adjusting devices being necessary.

EXAMPLES

Without further elaboration, it is believed that one skilled in the art can, using the preceding description, utilize the present invention to its fullest extent. The following preferred specific embodiments are, therefore, to be construed as merely illustrative, are not limitative of the remainder of the disclosure in any way whatsoever. In the following examples, all temperatures are set forth uncorrected in degrees Celsius; unless otherwise indicated, all parts and percentages are by weight.

EXAMPLE 1

Determination of anti-(human serum albumin)

(a) Silanization of silicon platelets

Silicon platelets (10×5×0.3 mm) were left to stand in a solution of 10% of dichlorodimethylsilane in trichloroethylene for 10 minutes and were then washed with trichloroethylene.

(b) Coating with human serum albumin (HSA)

The silanized platelets were left to stand in a 1% solution of HSA in saline (0.15M sodium chloride solution) for 30 minutes and then washed with distilled water.

(c) Incubation with rabbit anti-HSA serum (anti-HSA)

The silicon platelets coated with a monolayer of HSA were incubated with 10% of normal rabbit serum in various dilutions of rabbit anti-HSA serum in phosphate-buffered saline (pH 7.4) for 1 hour and were then washed with distilled water and dried in a stream of nitrogen.

(d) Evaluation

The platelets were irradiated with light (546 nm), polarized parallel to the plane of incidence, at an angle of incidence of 76.13°, and the intensity of the reflected light was measured with a photosensitive receiver.

As can be seen from the table which follows, the intensity of light measured is proportional to the concentration of the antiserum.

| Dilution of the antiserum | Measurement units |
| --- | --- |
| 1:8 | 130.35 |
| 1:16 | 120.67 |
| 1:32 | 85.01 |
| 1:64 | 60.99 |
| 1:128 | 40.28 |
| 1:256 | 20.37 |

EXAMPLE 2

Determination of anti-(human fibrinogen)

The silicon platelets were silanized as described in Example 1(a). Coating with human fibrinogen was carried out as described in Example 1(b), a 0.1% fibrinogen solution being used instead of a 1% HSA solution. Incubation with goat's anti-(human fibrinogen) was carried out as described in Example 1 (c), antiserum from goats being used here against the fibrinogen.

The platelets were evaluated as described in Example 1(d). In this case also, the light intensity measured is proportional to the concentration of the antiserum, as shown in the table which follows.

| Dilution of the antiserum | Measurement units |
| --- | --- |
| 1:8 | 201.77 |
| 1:16 | 120.03 |
| 1:32 | 94.68 |
| 1:64 | 70.55 |
| 1:128 | 59.19 |

EXAMPLE 3

Determination of anti-(human serum albumin)

To apply a layer of oxide to silicon platelets, the silicon platelets were first left to stand at 900° C. in an oven for 30 minutes, under a stream of oxygen gas. The oven was then flushed with argon gas at 900° C. for a further 5 minutes. Silanization of the silicon platelets thus treated, coating with HSA and incubation with anti-HSA were carried out as described in Example 1(a)–(c).

The platelets were evaluated as described in Example 1(d). An additional measurement of reflected light was done with a platelet having just the oxide layer. This reading was taken as a blank value and substracted from the readings of the platelets having antigen-antibody layers. The table which follows shows that application of a layer of oxide about 120 Å thick is associated with an increase in sensitivity.

| Dilution of the antiserum | Measurement units |
| --- | --- |
| 1:15 | 51.33 |
| 1:30 | 32.75 |
| 1:60 | 19.61 |
| 1:120 | 12.94 |
| 1:240 | 9.53 |
| 1:480 | 3.11 |

EXAMPLE 4

Cross-reaction with fibrinogen-silicon platelets

The silicon platelets were silanized as described in Example 1(a), and subsequent coating with fibrinogen was carried out as described in Example 2(b). To investigate the cross-reaction of anti-fibrinogen and anti-HSA, the platelets coated with fibrinogen were incubated with anti-HSA or anti-fibrinogen as described in Example 1(c).

The platelets were evaluated as described in Example 1(d). As can be seen from the table which follows, no increase in the light intensity is to be recorded with the platelets incubated with anti-HSA.

| Dilution of the antiserum | Measurement units |
| --- | --- |
| (anti-fibrinogen) | |
| 1:8 | 75.75 |
| 1:16 | 63.18 |
| 1:32 | 50.37 |
| (anti-HSA) | |
| 1:8 | 1.01 |
| 1:16 | 0.51 |
| 1:32 | 2.34 |

EXAMPLE 5

Determination of human serum albumin (HSA) by the sandwich method

The silicon platelets were silanized as described in Example 1(a). For coating with anti-HSA, the silanized platelets were left to stand in a solution for 100 μ/ml of anti-HSA-IgG in saline for 2 hours and were then washed with distilled water. The paltelets thus coated were then left to stand with 0.1% of bovine serum albumin in solutions of various concentrations of HSA in phosphate buffer (pH 7.4) for 1 hour and were subsequently washed with phosphate buffer. Incubation with anti-HSA serum was carried out as described in Example 1(c), the antiserum being diluted in the ratio 1:8 and the incubation time being 3 hours.

The platelets were evaluated as described in Example 1(d). As can be seen from the table which follows, the light intensity measured correlates with the amount of HSA in the incubation solution.

| HSA [μg/ml] | Measurement units |
| --- | --- |
| 2.40 | 142.50 |
| 1.60 | 128.89 |
| 1.20 | 114.31 |
| 1.00 | 98.26 |
| 0.80 | 86.99 |
| 0.60 | 70.02 |

-continued

| HSA [μg/ml] | Measurement units |
| --- | --- |
| 0.40 | 46.76 |
| 0.20 | 24.17 |
| 0.10 | 15.32 |
| 0.05 | 6.68 |

EXAMPLE 6

Determination of HSA by the sandwich method using an anti-HSA-ferritin conjugate.

Silanization of the silicon platelets, coating with anti-HSA and incubation with HSA were carried out as described in Example 5. Incubation with anti-HSA-ferritin conjugate was carried out as described in Example 1(c), the solution of antibody conjugated with ferritin being diluted in the ratio 1:10.

The platelets were evaluated as described in Example 1(d). As can be seen from the table which follows, the light intensity measured correlates with the amount of HSA in the incubation solution.

| HSA [μg/ml] | Measurement units |
| --- | --- |
| 1.30 | 202.44 |
| 0.80 | 148.51 |
| 0.40 | 87.97 |
| 0.20 | 50.03 |
| 0.10 | 28.59 |
| 0.05 | 18.18 |
| 0.025 | 7.23 |

EXAMPLE 7

Determination of human serum albumin (HSA) by the competing method

Silanization of the silicon platelets and coating with HSA were carried out as described in Example 1(a) and 1(b). For incubation with HSA and anti-HSA, a dilution series of human sera in phosphate buffer containing 1% of bovine serum albumin was first prepared. 0.25 ml of anti-HSA (5 mg of antibody/ml of phosphate buffer) was added to 1 ml of the particular dilution, and the platelets prepared according to Example 1(a) were immersed in this solution. After an incubation time of 3 hours, the platelets were washed and dried.

The platelets were evaluated as described in Example 1(d). As can be seen from the table which follows, the measurement signal is inversely proportional to the concentration of human serum. An anti-HSA-ferritin conjugate could be used in a similar manner, instead of anti-HSA.

| Dilution of the human serum | Measurement units |
| --- | --- |
| 1:8 | 18.62 |
| 1:16 | 41.08 |
| 1:32 | 60.00 |
| 1:64 | 81.93 |
| 1:128 | 109.19 |
| 1:256 | 128.94 |

EXAMPLE 8

Determination of L-thyroxin by the competing method

The silicon platelets were silanized as described in Example 1(a). To prepare an L-thyroxin-ferritin conjugate, 500 mg of ferritin were dissolved in 250 ml of distilled water, and 10 mg of L-thyroxin (sodium salt) were added. 12 mg of N-ethyl-N'-(3-dimethylaminopropyl)-carbodiimide in 5 ml of water were added to the solution at a pH value of 5.5 and the mixture was stirred for 30 minutes. The reaction product was dialysed ten times against 5 liters of water containing 0.9% of benzyl alcohol. After centrifugation, the solution was lyophilized. The platelets were then coated with a solution of 100 μg/ml of rabbit anti-L-thyroxin antibodies as described in Example 1(b). For incubation with L-thyroxin and L-thyroxin-ferritin conjugate, a dilution series (5–100 ng/ml) of L-thyroxin in phosphate buffer containing 1% of bovine serum albumin (in each case 1 ml) was first prepared. The platelets coated with anti-L-thyroxin were introduced into these solutions and incubated for 2 hours. 20 μl of a solution of L-thyroxin-ferritin conjugate (1 mg/ml) was then added, and incubation was carried out for a further 2 hours. The platelets were then washed and dried.

The platelets were measured as described in Example 1(d). From the table which follows, it can be seen that the concentration of L-thyroxin is inversely proportional to the light intensity.

| L-thyroxin [ng/ml] | Measurement units |
| --- | --- |
| 100 | 5.33 |
| 80 | 6.10 |
| 60 | 8.05 |
| 40 | 10.96 |
| 20 | 14.49 |
| 10 | 17.71 |
| 5 | 19.83 |

EXAMPLE 9

Determination of human immunoglobulin (h-IgG) by the sandwich method using immuno-beads of rabbit anti-(human-IgG) (a-h-IgG)

The silicon platelets were silanized as described in Example 1(a). For coating with rabbit anti-(human IgG), the silanized platelets were left to stand in a solution of 100 μg/ml of a-h-IgG in saline for 2 hours and were then washed with distilled water. The platelets thus coated were then left to stand in solutions of various concentrations of IgG in phosphate buffer (pH 7.4) containing 0.1% of bovine serum albumin for 1 hour, and were then washed with phosphate buffer. Incubation with immuno-beads of rabbit anti-(human-IgG) was carried out as described in Example 1(c), the immuno-beads being used in a concentration of 1 mg/ml. The system was incubated for 3 hours, with continuous shaking.

Evaluation was carried out as described in Example 1(d). As can be seen in the table which follows, the light intensity measured correlates with the amount of h-IgG in the incubation solution.

| h-IgG [ng/ml] | Measurement units |
| --- | --- |
| 80.0 | 172.51 |
| 40.0 | 115.10 |
| 20.0 | 71.82 |
| 10.0 | 42.18 |
| 5.0 | 28.33 |
| 2.5 | 16.71 |
| 1.0 | 8.27 |
| 0.5 | 5.06 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the quantitative determination of a component of an organic system comprising a specifically bonding receptor component and a substance component which can be specifically bonded by the receptor, comprising
    incubating one of the components, after it has been immobilized on the surface of a material having a refractive index effectively different from that of the organic system, with the other specific component;
    irradiating said surface with an effective beam of electromagnetic radiation which is polarized parallel to the plane of incidence, the angle of incidence of the radiation being approximately equal to or equal to the angle $\Phi$ at which the intensity of the radiation reflected from said surface, prior to said immobilization, reaches a minimum; and measuring the intensity of the reflected radiation as a measure of the concentration to be determined.

2. A method of claim 1 wherein the incubation step is carried out in the presence of an additional bonding specific component.

3. A method of claim 1 wherein said surface, having said minimum point in said reflected intensity curve, is precoated with an oxide layer or a polymer film, or by silanization.

4. A method of claim 1 wherein said surface has a refractive index greater than 2.

5. A method of claim 1 wherein said material is a semiconductor, dielectric, or metal or a carrier coated therewith.

6. A method of claim 5 wherein said material is silicon or a carrier coated with silicon.

7. A method of claim 1 wherein the organic system is an antigen/hapten-antibody system.

8. A method of claim 1 further comprising irradiating a second identical surface of material which has not been incubated with a second beam of said electromagnetic radiation; measuring the reflected intensities of the two beams; and determining the concentration of the component to be determined from the difference between the two reflected intensities.

9. A method of claim 1 comprising irradiating materials coated with various receptor or substance components with multiple beams; and simultaneously determining the concentration of each component by measuring the intensities of the reflected beams.

10. A method of claim 2 wherein said additional component bonds to one of said receptor or substance components.

11. A method of claim 2 wherein the additional bonding specific component is labelled.

* * * * *